(12) United States Patent
Amao et al.

(10) Patent No.: US 8,802,896 B2
(45) Date of Patent: Aug. 12, 2014

(54) POLYETHER COMPOUND, CURING AGENT USING THE POLYETHER COMPOUND, AND PRODUCING METHOD OF THE POLYETHER COMPOUND

(71) Applicant: Fujifilm Corporation, Tokyo (JP)

(72) Inventors: Akihito Amao, Kanagawa (JP); Hirotaka Kitagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/042,357

(22) Filed: Sep. 30, 2013

(65) Prior Publication Data

US 2014/0100390 A1     Apr. 10, 2014

Related U.S. Application Data

(63) Continuation of application No. PCT/JP2012/057506, filed on Mar. 23, 2012.

(30) Foreign Application Priority Data

Mar. 30, 2011   (JP) ................................ 2011-074662
Mar. 30, 2011   (JP) ................................ 2011-074663

(51) Int. Cl.
| | | |
|---|---|---|
| *C07C 217/42* | (2006.01) | |
| *C07C 231/06* | (2006.01) | |
| *C07C 233/05* | (2006.01) | |
| *C07C 235/08* | (2006.01) | |
| *C07C 237/08* | (2006.01) | |
| *C07C 209/48* | (2006.01) | |
| *C07C 211/13* | (2006.01) | |
| *C07C 43/02* | (2006.01) | |

(52) U.S. Cl.
USPC ........... 564/504; 564/124; 564/130; 564/123; 564/153; 564/491; 564/512; 568/589

(58) Field of Classification Search
USPC ......... 564/123, 124, 130, 153, 491, 504, 512; 568/589
See application file for complete search history.

(56) References Cited

U.S. PATENT DOCUMENTS

| 5,241,016 A | 8/1993 | Waddill et al. |
| 2008/0160017 A1 | 7/2008 | Baker et al. |
| 2010/0069672 A1 | 3/2010 | Burton et al. |
| 2012/0184778 A1 | 7/2012 | Burton et al. |

FOREIGN PATENT DOCUMENTS

| CN | 101675084 A | 3/2010 |
| JP | 06-073357 A | 3/1994 |
| JP | 2007-031372 A | 2/2007 |
| JP | 2010-521563 A | 6/2010 |
| WO | 2005/113605 A1 | 12/2005 |
| WO | 2008/112952 A1 | 9/2008 |

OTHER PUBLICATIONS

Cho, J. K.; Kim, D-W.; Namgung, J.; Lee, Y-S. "Preparation of tris-based dendrimer-grafted core-shell type resin for solid-phase peptide synthesis" Tetrahedron Letters 42 (2001) p. 7443-7445.*
International Search Report; PCT/JP2012/057506; Apr. 24, 2012.
Written Opinion of the International Searching Authority; PCT/JP2012/057506; Apr. 24, 2012.
The first Notice of the Opinion on Examination issued by the Chinese Patent Office on Feb. 21, 2014, which corresponds to Chinese Patent Application No. 201280015689.4 and is related to U.S. Appl. No. 14/042,357; with English language tanslation.
J.J.Lin, et al.; "N,N'-dialkyl polyether amine is set as a protected isocyanate hardener"; China Academic Journal Electronic Publishing House; Dec. 31, 2003; Zhanjie 2003, 24(5); pp. 43-45; Coking vol. 25, No. 4.

* cited by examiner

*Primary Examiner* — Jafar Parsa
*Assistant Examiner* — Amy C Bonaparte
(74) *Attorney, Agent, or Firm* — Studebaker & Brackett PC

(57) ABSTRACT

Disclosed is a polyether compound which is useful as a curing agent or the like, a curing agent using the compound and a producing method of the compound. The polyether compound of the present invention is represented by the following general formula (1).

General Formula (1)

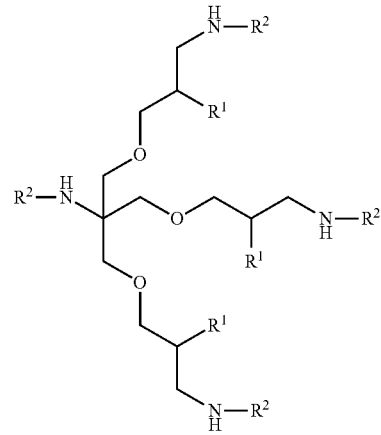

(In the formula, $R^1$ represents a hydrogen atom or a methyl group and $R^2$ represents a hydrogen atom or —C(=O)—C($R^3$)=CH$_2$. $R^3$ represents a hydrogen atom or a methyl group. $R^1$, $R^2$ and $R^3$ may be the same as or different from each other.)

7 Claims, 11 Drawing Sheets

POLYETHER COMPOUND, CURING AGENT USING THE POLYETHER COMPOUND, AND PRODUCING METHOD OF THE POLYETHER COMPOUND

BACKGROUND OF THE INVENTION

1. Field of the Invention

The present invention relates to a polyether compound, a curing agent using the polyether compound and a producing method of the polyether compound.

2. Description of the Related Art

As a raw material of various kinds of polymers and curable resin compositions, a polymerizable compound which is polymerized and cured by imparting energy such as heat and light, is widely used for industrial uses such as coating materials, paints, printing inks, adhesive agents and resist materials.

For example, an epoxy resin (an epoxy compound) is used in various fields such as an adhesive agent for civil engineering and constructions, a sealing agent for semiconductors, an insulating material for printed circuit boards, mold devices for high voltage power, or the like, paints for cans, automobiles, or the like due to its excellent characteristics and diversity.

It is possible to improve the characteristics of an obtained molded body (a cured product) by using a polymerizable compound. For example, by the compound being polymerized to be a cured film by heating after an image is formed by using inks or paints containing a polymerizable compound which is cured by heat, an image which has an excellent weather resistance and durability can be created.

Curing of the polymerizable compound can be conducted by using a curing agent together with a polymerizable compound. As a curing agent, for example, a polymerizable compound containing an acrylamide group such as N,N-methylenebisacrylamide is included (refer to Handbook of crosslinking agent, edited by Shinzo Yamashita and Tosuke Kaneko, published by Taisei Co.).

In addition, the curing agents used for curing of the epoxy compound are diverse depending on the applications. For example, as a polyaddition-type curing agent, polyamine compounds such as aliphatic polyamines, alicyclic polyamines and aromatic polyamines are included (refer to Edited by the Japan Society of Epoxy Resin Technology, Volume 1 Fundamentals I review epoxy resin, the Japan Society of Epoxy Resin Technology, p 123-146 (2003)).

Aliphatic polyamines, especially, are used as a normal-temperature curing type curing agent since the curing properties are high. A cured product which is obtained by using an aliphatic polyamine has excellent mechanical properties as well as excellent adhesive properties and chemical resistance. As such aliphatic polyamines, diethylenetriamine, triethylenetetramine, trimethyl hexamethylene diamine, 2-methyl pentamethylene diamine, and the like are included.

On the other hand, development of new curing agents using novel compounds has been desired.

SUMMARY OF THE INVENTION

The present invention provides a polyether compound which is useful as a curing agent or the like, a curing agent using the compound and a producing method of the polyether compound. More specifically, the present invention provides a novel polyamine compound, an epoxy curing agent using the compound and a producing method of the compound. In addition, the present invention provides a novel polymeizable compound (a polyfunctional compound) and a curing agent using the compound.

According to the present invention for solving the problem described above, there is provided a polymer compound which is represented by the following general formula (1).

[Chem. 1]

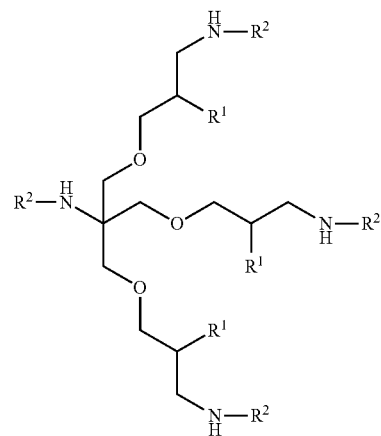

General Formula (1)

(In the formula, represents a hydrogen atom or a methyl group and $R^2$ represents a hydrogen atom or —C(C=O)—C($R^3$)=$CH_2$. $R^3$ represents a hydrogen atom or a methyl group. $R^1$, $R^2$ and $R^3$ may be the same as or different from each other.)

In the present invention, $R^2$ may represent a hydrogen atom, $R^1$ may represent a hydrogen atom and $R^2$ may represent —C(=O)—C($R^3$)=$CH_2$ in the general formula (1) described above.

According to the present invention, there is provided a curing agent using the polyether compound described above.

In addition, according to the present invention, there is provided a producing method of a polyether compound represented by the following general formula (3) including a step of obtaining a compound represented by the following general formula (2) by reacting tris(hydroxymethyl)aminomethane with acrylonitril and/or methacrylonitril and a step of reducing the compound represented by the general formula (2).

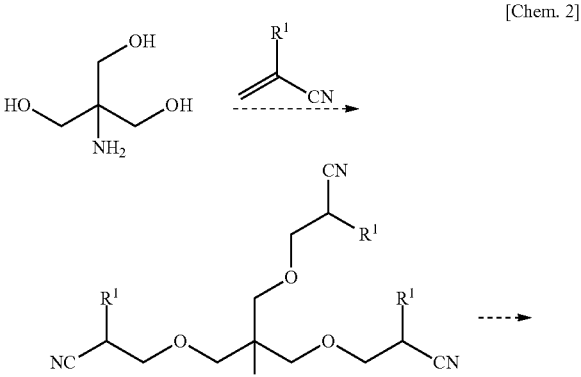

[Chem. 2]

General Formula (2)

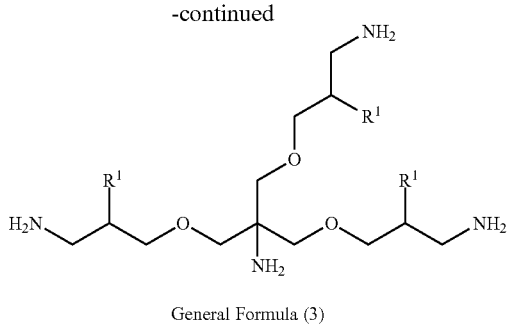

General Formula (3)

(In the formula, $R^1$ represents a hydrogen atom or a methyl group. $R^1$ may be the same as or different from each other.)

According to the present invention, it is possible to provide a polyether compound having an excellent polymerizing ability and/or curing ability.

DESCRIPTION OF THE PREFERRED EMBODIMENTS

Figure 1:
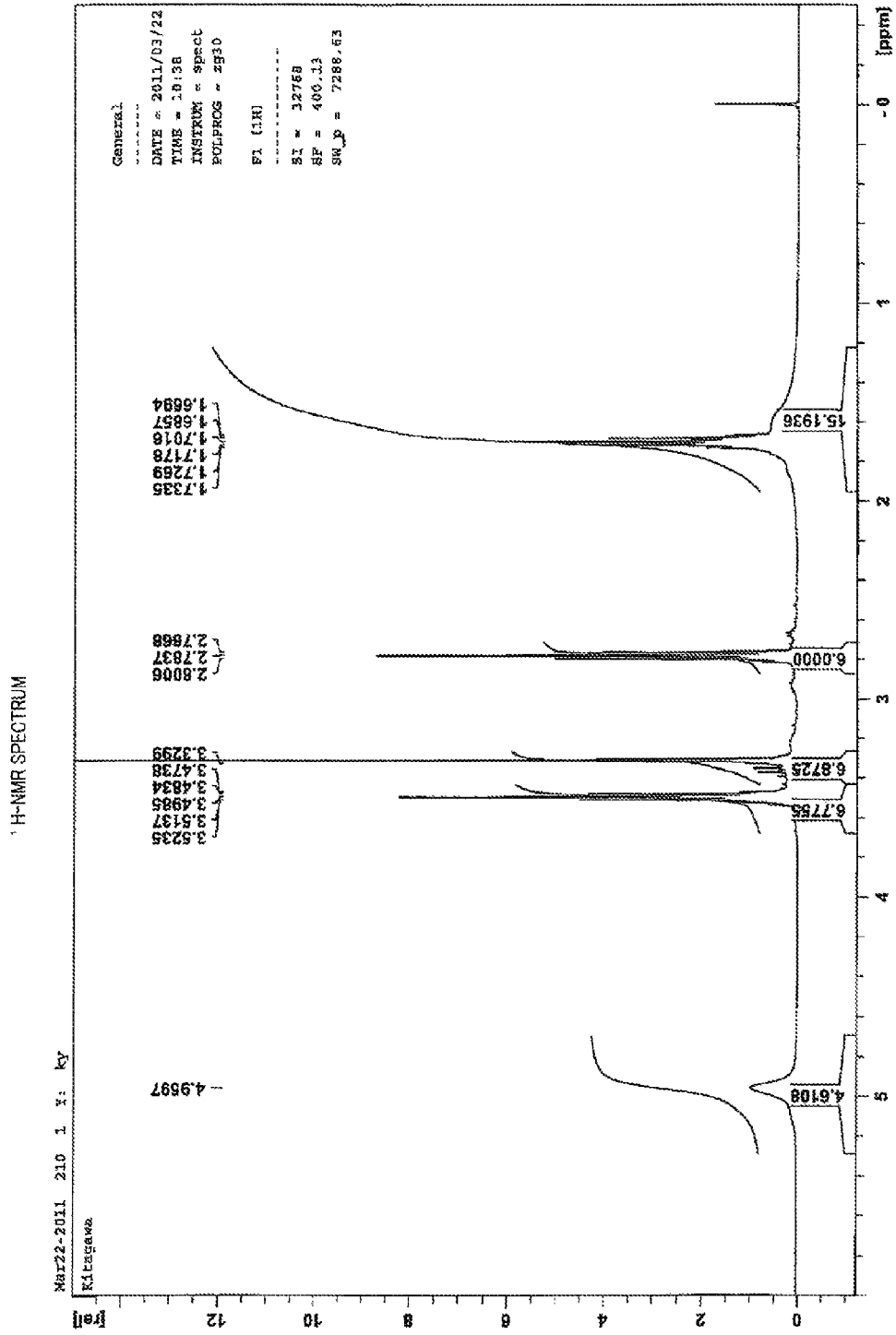
FIG. 1 is a diagram of a $^1$H-NMR spectrum chart of a polyamine compound (1) which was synthesized in Example 1.

A polyether compound in the present invention is represented by the following general formula (1).

[Chem. 3]

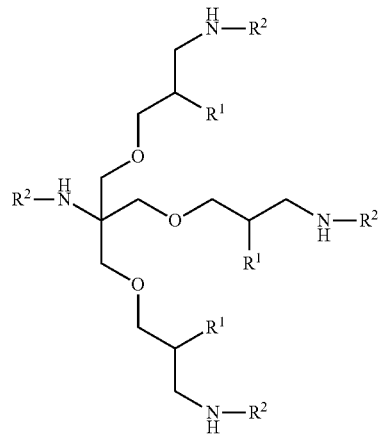

General Formula (1)

(In the formula, $R^1$ to $R^3$ are the same as $R^1$ to $R^3$ described above.)

(Polyamine Compound)

As an aspect of a polyether compound in the present invention, for example, a polyether compound (more specifically, a polyamine compound) represented by the following general formula (3) in which $R^2$ in the general formula (1) described above is a hydrogen atom, is included. In the present invention, $R^1$ is preferably a hydrogen atom.

[Chem. 4]

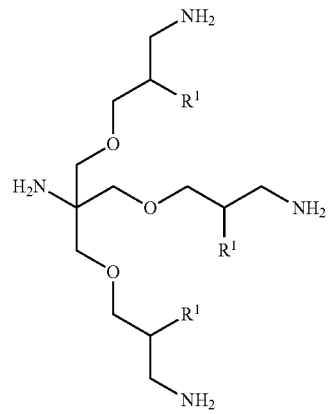

General Formula (3)

(In the formula, $R^1$ is the same as $R^1$ described above.)

The polyamine compound represented by the general formula (3) has four amino groups, particularly, primary amino groups having high reactivity ($-NH_2$) in a molecule, and these amino groups are sterically distributed with a specific distance in molecular structure. Therefore, the polyamine compound has an excellent performance as an epoxy curing agent.

When mixed with an epoxy compound, the polyamine compound (the epoxy curing agent) represented by the general formula (3) causes a polyaddition-type reaction to cure and form a so called epoxy resin. When the epoxy resin is formed, the polyamine compound represented by the general formula (3) may be used alone or may be used in combination of at least one kind of a well-known curing agent or a curing accelerator except for the polyamine compound represented by the general formula (3). In a case where the well-known curing agent, or the like is used together, these well-known curing agents, or the like may be contained in the polyamine compound (the epoxy curing agent) represented by the general formula (3).

As a well-known curing agent that may be used together, aliphatic polyamines, alicyclic polyamines, aromatic polyamines, special polyamines, and the like are included. As aliphatic polyamines, diethylenetriamine, triethylenetetramine, tetraethylenepentamine, m-xylene diamine, trimethyl hexamethylene diamine, 2-methyl pentamethylene diamine, diethylaminopropylamine, and the like are included. As alicyclic polyamines, isophorone diamine, 1,3-bisaminomethylcyclohexane, bis(4-aminocyclohexyl)methane, norbornene diamine, 1,2-diaminocyclohexane, bis(4-amino-3-methyl cyclohexyl)methane, and the like are included. As aromatic polyamines, diaminodiphenylmethane, m-phenylenediamine, diaminodiphenyl sulfone, and the like are included. As special polyamines, polyoxypropylene diamine, polyoxypropylene triamine, polycyclohexyl polyamine mixture, 3,9-bis(3-aminopropyl)-2,4,5,10-tetraspiro[5.5]undecane, N-aminoethyl piperazine, and the like are included.

As a well-known curing accelerator that may be used together, fatty acids, benzoic acids, alcohols, phenols, mercaptos, and the like are included. Specifically, compounds described in Table 5 in Section 2 of Chapter 3, edited by the Japan Society of Epoxy Resin Technology, Volume 1 Fundamentals I review epoxy resin, the Japan Society of Epoxy Resin Technology (2003) are included.

In a case where the polyamine compound (the epoxy curing agent) represented by the general formula (3) is used with these well-known curing agents, or the like together, while being different depending on the object for using and the epoxy compound which is used, the used amount of the well-known curing agents, or the like is preferably less than 50 parts by mass and more preferably less than 25 parts by mass, with respect to 100 parts by mass of the polyamine compound (the epoxy curing agent) represented by the general formula (3), and the polyamine compound (the epoxy curing agent) represented by the general formula (3) is even more preferably used alone.

As an epoxy compound which is used to form an epoxy resin, the well-known epoxy compounds which are glycidyl ether type, glycidyl ester type, glycidyl amine type, oxidized type, and the like, are included.

As the glycidyl ether type, a Bis-A type epoxy compound, a Bis-F type compound, a High-Br type epoxy compound, a novolac type epoxy compound, an alcohol type epoxy compound are included. As the glycidyl ester type, a hydrophthalic acid type epoxy compound, a dimer acid type epoxy compound are included. As the glycidyl amine type, an aromatic amine type epoxy compound, and an aminophenol type epoxy compound are included. As the oxidized type, an alicyclic epoxy compound is included.

When A=(the blending amount of polyamine/the active hydrogen equivalent)/(the blending amount of epoxy/the epoxy equivalent), the ratio of the blending amount of the polyamine compound represented by the general formula (3) and the epoxy compound is preferably in the range of $0.1<A<10$, more preferably $0.5<A<2$, even more preferably $0.8<A<1.2$.

Here, the active hydrogen equivalent is the value obtained by dividing the molecular weight of the polyamine compound by the number of hydrogen atoms of the amino groups. In addition, the epoxy equivalent is the value obtained by dividing the molecular weight of the epoxy compound by the number of the epoxy groups.

The polyamine compound of the present invention can be preferably used as a curing agent of an epoxy compound which is used for an adhesive agent for civil engineering and constructions, a sealing agent for semiconductors, an insulating material for printed circuit boards, mold devices for high voltage power, or the like, paints for cans, automobiles, or the like.

(Producing Method of Polyamine Compound)

A producing method of the polyether compound (more specifically, the polyamine compound) represented by the general formula (3) is not particularly limited, however, for example, a method of production through a step of obtaining a compound represented by the following general formula (2) by reacting tris(hydroxymethyl)aminomethane with acrylonitril and/or methacrylonitril (the first step) and a step of reducing a compound represented by the general formula (2) (the second step) is included.

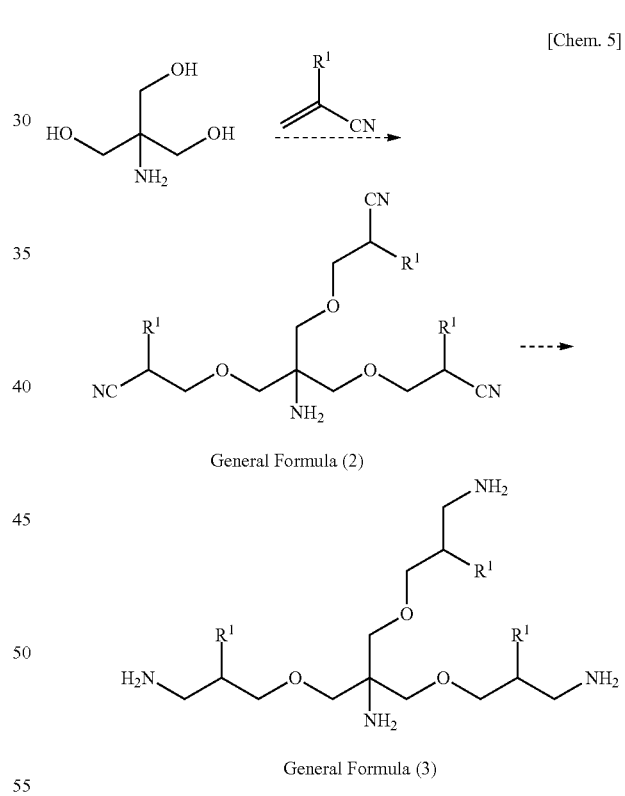

[Chem. 5]

General Formula (2)

General Formula (3)

(In the formula, $R^1$ is the same as $R^1$ described above.)

[First Step]

In the first step, a compound represented by the general formula (2) is obtained by allowing Michael addition reaction of a hydroxyl group of tris(hydroxymethyl)aminomethane with respect to acrylonotrile and/or methacrylonitrile in the presence of a base. Michael addition reaction may be conducted in homogeneous reaction or in two phase system reaction, however, it is preferred that it be conducted in homogeneous reaction from the viewpoint of suppressing the forming of by-product.

Homogeneous reaction may be either a method of conducting the reaction in the absence of solvent by using a largely excessive amount of acrylonotrile and/or methacrylonitrile or a method of conducting the reaction by using a solvent, however, the method of conducting the reaction by using a solvent is preferred to control the reaction temperature.

As a preferred solvent, an aromatic-based solvent such as toluene, a nitrile-based solvent such as acetonitrile, an ether solvent such as tetrahydrofuran, an amide-based solvent such as N,N-dimethylacetamide and a sulfoxide-based solvent such as dimethyl sulfoxide are included. Among these, from the viewpoint of the solubility of tris(hydroxymethyl)aminomethane as a raw material and the solvent distillation after the reaction, an aromatic-based solvent, a nitrile-based solvent and an ether-based solvent are more preferable, toluene, acetonitrile and tetrahydrofuran are even more preferable, and toluene and acetonitrile are particularly preferable.

As a base used in the first step, a strong base in which pKa of the conjugate acid is 13 or more is included. As such a strong base, a hydroxide such as sodium hydroxide and potassium hydroxide, a metal alkoxide such as sodium methoxide, sodium t-butoxide and potassium t-butoxide, a metal hydride such as sodium hydride, an organic strong base such as guanidine and DBU, and the like are included. Among these, a metal alkoxide (the conjugate base of the tertiary alcohol) such as sodium t-butoxide and potassium t-butoxide and a hydroxide such as potassium hydroxide are preferable from the viewpoint of suppressing the forming of by-product. In a case of using a metal alkoxide as a base, the addition amount of the base is preferably from 0.00001 to 1.0 mol, further preferably from 0.00001 to 0.5 mol, more preferably from 0.0001 to 0.1 mol, even more preferably from 0.0005 to 0.05 mol and particularly preferably 0.0005 to 0.002 mol, with respect to 1 mol of tris(hydroxymethyl)aminomethane. In a case of using a hydroxide as a base, the addition amount of the base is preferably from 0.1 to 2 mol and more preferably from 0.5 to 1 mol.

In a case of conducting the reaction in the absence of solvent, the addition amount of acrylonitrile and/or methacrylonitrile is preferably in the range of 3 to 30 mol, more preferably from 4 to 10 mol, particularly preferably from 5 to 8 mol, with respect to 1 mol of tris(hydroxymethyl)aminomethane. In a case of conducting the reaction by using a solvent, the range of 3 to 12 mol is preferable, from 3.3 to 10 mol is more preferable and from 3.6 to 8 mol is particularly preferable, with respect to 1 mol of tris(hydroxymethyl)aminomethane.

The reaction temperature is preferably in the range of −20° C. to 90° C., more preferably from 0° C. to 80° C., and particularly preferably from 20° C. to 70° C., from the viewpoint of shortening the reaction time and suppressing the side reaction. The reaction time is preferably from 30 minutes to 8 hours.

The reaction atmosphere may be either the atmosphere or the inert gas, however, the inert gas is preferable in order to avoid that the base is deactivated by carbon dioxide in the atmosphere. As the inert gas, nitrogen, argon, and the like are included.

After the reaction is finished, it is preferred that a compound in which pKa is 12 or less be added to stop the reaction. The compounds are not particularly limited as long as they are a compound in which pKa is 12 or less, however, an inorganic compound such as sodium hydrogen carbonate and sodium hydrogen sulphate is preferable since the post-treatment is simple. The stopping of the reaction is preferably conducted after the reaction solution is cooled to 30° C. or less, more preferably conducted at 20° C. or less and even more preferably conducted at 10° C. or less.

[Second Step]

In the second step, a nitrile group of the intermediate represented by the general formula (2) described above is reduced to an amino group. It dose not matter in any reduction reaction, however, this reduction reaction in the present invention is preferably the hydrogenation reaction.

The hydrogenation reactions are not particularly limited as long as they are a well-known method, however, for example, the heterogeneous system catalytic hydrogenation reaction is included.

As a catalyst which is used in the heterogeneous system catalytic hydrogenation reaction, a Raney catalyst such as Raney nickel and Raney cobalt and a supported catalyst in which a catalytic metal such as palladium, platinum, rhodium and ruthenium is supported on a support such as carbon are included. Among them, a Raney catalyst is preferable from the viewpoint of reaction selectivity.

As a solvent used in the second step, water or an alcohol-based solvent is preferable, a co-solvent of water and an alcohol is more preferable, and a co-solvent of water and methanol is even more preferable.

It is preferred to make ammonia coexist in the reaction solution in order to suppress the side reaction. The ammonia addition method may be either a method of adding aqueous ammonia as a solvent or a method of introducing ammonia gas. The addition amount of ammonia is preferably 1 mol/kg or more, more preferably 3 mol/kg or more, and particularly preferably 5 mol/kg or more, with respect to the reaction solution.

Hydrogen pressure is not particularly limited and it is possible to conduct with 0.1 to 12 MPa.

The reaction temperature is preferably in the range of 0° C. to 100° C., more preferably from 10° C. to 50° C., and particularly preferably from 20° C. to 35° C., from the viewpoint of shortening the reaction time and suppressing by-products. The reaction time is preferably from 2 hours to 20 hours.

(Polyfunctional Compound)

As another aspect of a polyether compound in the present invention, for example, a polyether compound (more specifically, a polyfunctional compound) represented by the following general formula (4) in which $R^2$ in the general formula (1) described above is —C(=O)—C($R^3$)=$CH_2$ is included. In the present invention, $R^1$ is preferably a hydrogen atom.

[Chem. 6]

General Formula (4)

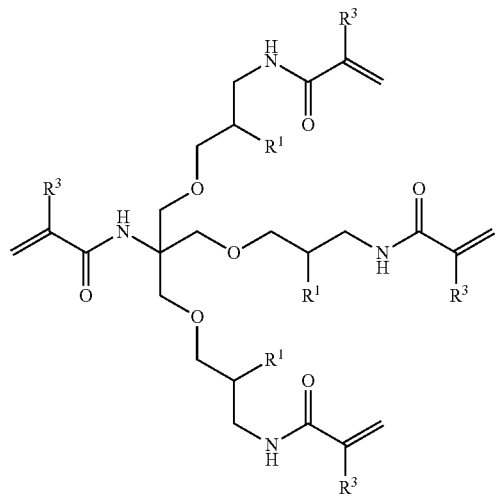

(In the formula, $R^3$ is the same as $R^3$ described above.)

The polyfunctional compound represented by the general formula (4) has four acrylamide groups or methacrylamide group as a polymerizable group in the molecule and has an excellent polymerizing ability and curing ability. The compound is polymerized by applying an active radiation such as σ-rays, γ-rays, X-rays, ultraviolet rays, visible rays, infrared light rays and an electron beam, and energy such as heat, and shows the curing properties.

The polyfunctional compound represented by the general formula (4) is suitably used as a thermosetting compound. For example, it is possible to obtain a thermosetting resin composition by blending a curing agent into the polyfunctional compound.

In addition, the polyfunctional compound represented by the general formula (4) can be used as a curing agent. Since the polyfunctional compound has an excellent curing ability, the curing agent using the polyfunctional compound has excellent curing properties and is suitably used in applications such as printing inks, various paints, resists, adhesive agents, coating materials, and the like. The curing agent using the polyfunctional compound represented by the general formula (4) may appropriately contain other curing agents, polymerization initiators, solvents, and the like according to the applications, and the like.

(Producing Method of Polyfunctional Compound)

A producing method of the polyether compound (more specifically, the polyfunctional compound) represented by the general formula (4) is not particularly limited, however, for example, a method of production through a step of obtaining a compound represented by the following general formula (2) by reacting tris(hydroxymethyl)aminomethane with acrylonitril and/or methacrylonitril (the first step), a step of obtaining a compound represented by the general formula (3) by reducing a compound represented by the general formula (2) (the second step), and a step of the acylation by reacting a compound represented by the general formula (3) with acrylic acid chloride and/or methacrylic acid chloride (the third step) is included.

[Chem. 7]

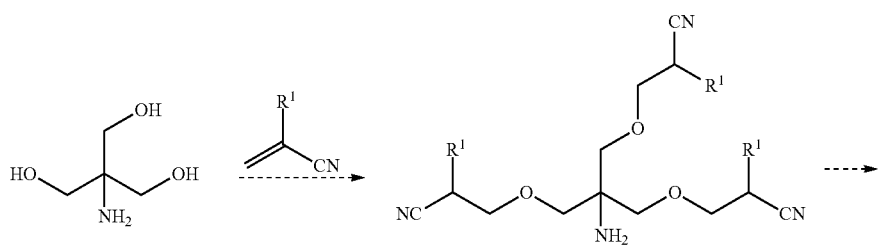

General Formula (2)

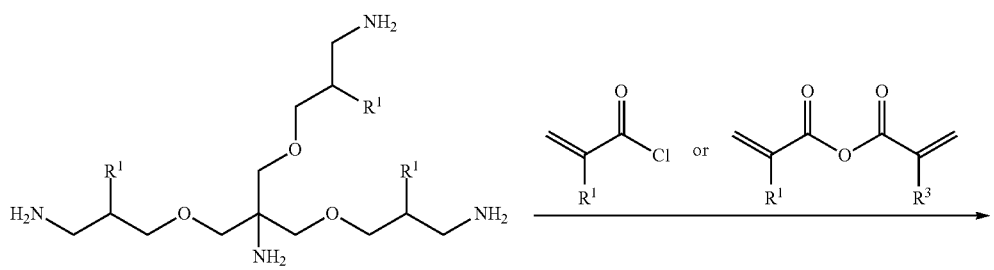

General Formula (3)

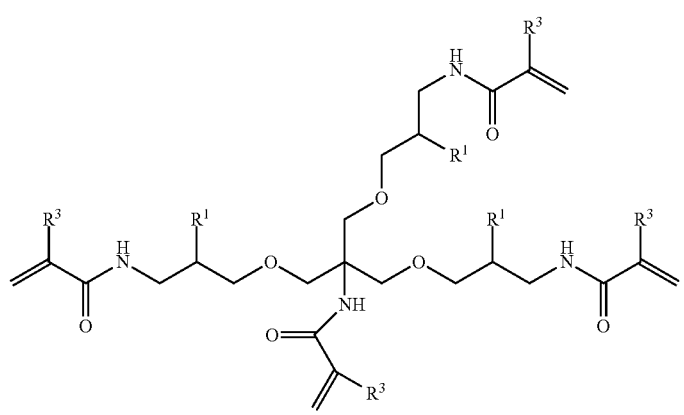

General Formula (4)

[First Step and Second Step]

Details of the first step and the second step are as described above.

[Third Step]

In the third step, a polymerizable group is introduced into the molecule by reacting acrylic acid chloride and/or methacrylic acid chloride under coexistence of a basic aqueous solution, with respect to an amino group of the polyamine compound represented by the general formula (3) described above. In the third step, by using both acrylic acid chloride and methacrylic acid chloride, it is possible to obtain a polyfunctional compound having an acrylamide group and a methacrylamide group as the final product in the same molecule.

In the third step, diacrylic anhydride and/or dimethacrylic anhydride may be used, instead of acrylic acid chloride and/or methacrylic acid chloride.

As a base used in the third step, sodium hydroxide, sodium carbonate, sodium hydrogen carbonate, and the like are included. The amount used of the base is preferably from 4.4 mol to 12.0 mol and more preferably from 6.0 mol to 8.0 mol, with respect to 1 mol of the polyamine compound represented by the general formula (3).

The third step is preferably conducted at −10° C. to 30° C. of the reaction temperature and for 30 minutes to 6 hours of the reaction time, from the viewpoint of shortening the reaction time and suppressing the side reaction.

The polyfunctional compound obtained in the third step and represented by the general formula (4) can be separated and collected from the reaction product liquid by a conventional method. For example, it is possible to collect by extraction operation using an organic solvent, crystallization using a poor solvent, column chromatography using silica gel, and the like.

EXAMPLE

Hereinafter, the present invention will be described in more detail base on examples, however, the present invention is not limited thereto. Here, unless otherwise specified, 'part' and '%' are based on mass.

Example 1

Synthesis of Polyamine Compound (1)

According to the following scheme, the polyamine compound (1) ($R^1$ is a hydrogen atom.) of the present invention, represented by the general formula (3), was synthesized.

[Chem. 8]

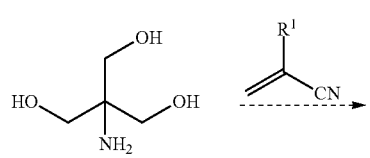

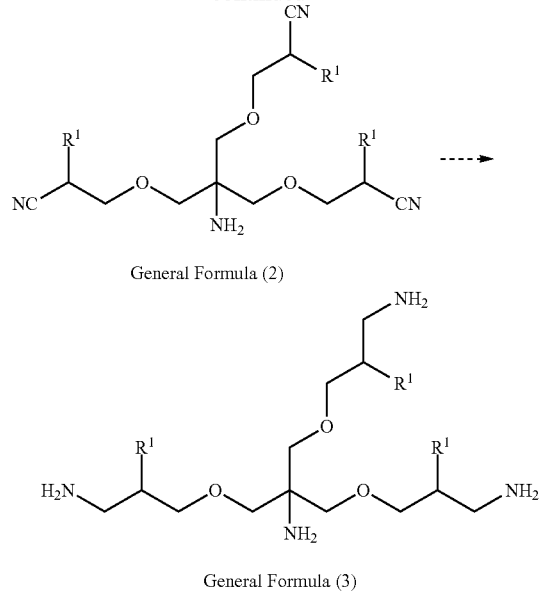

General Formula (2)

General Formula (3)

[First Step]

145.3 g (1.2 mol) of tris(hydroxymethyl)aminomethane, 115 mg (1.2 mmol) of sodium t-butoxide and 1.2 L of acetonitrile were added into a three-necked flask with a volume of 3 L and heated up to 55° C. with stirring under a nitrogen flow. After 286.7 g (5.4 mol) of acrylonitrile was added dropwise over 30 minutes thereto, the reaction solution was stirred at 55° C. for 1 hour until it became uniform. Thereafter, the reaction solution was cooled to 20° C. and stirred for 1 hour, then further cooled to 0° C. and stirred for 4 hours Next, after 6.0 g of sodium hydrogen carbonate was added to stop the reaction while stirring at 0° C., mineral salts were removed by filtering being performed. 343.3 g of the intermediate ($R^1$ is a hydrogen atom.) represented by the general formula (2) was obtained by the filtrate being concentrated under a reduced pressure.

[Second Step]

24.0 g of the obtained intermediate, 48.0 g of the Ni catalyst (Raney nickel 2400, manufactured by W. R. Grace & Co.), 300 ml of methanol, and 300 ml of 25% aqueous ammonia were put into an autoclave with a volume of 1 L and sealed. After replacing with nitrogen twice inside the autoclave, hydrogen of 10 Mpa was introduced and the reaction was performed at 25° C. for 16 hours. After the reaction was finished, the reaction liquid was taken out after replacing with nitrogen inside the autoclave. After filtering the Ni catalyst in the reaction liquid by Celite filtration, 23.8 g of the polyamine compound (1) of the present invention, represented by the general formula (3) was obtained by the filtrate being concentrated under reduced pressure.

Figure 2:
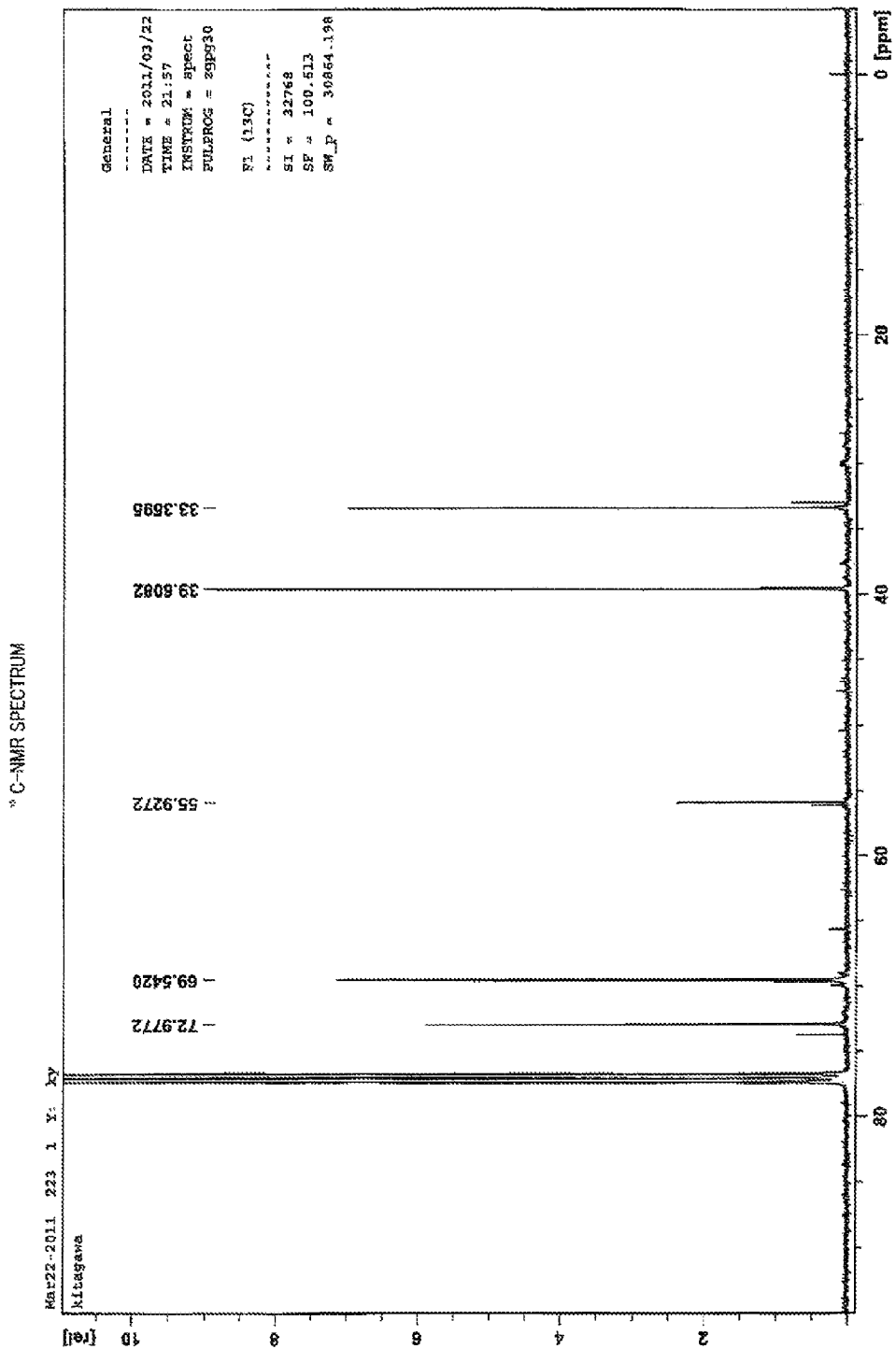
FIG. 2 is a diagram of a $^{13}$C-NMR spectrum chart of a polyamine compound (1) which was synthesized in Example 1.
Figure 3:
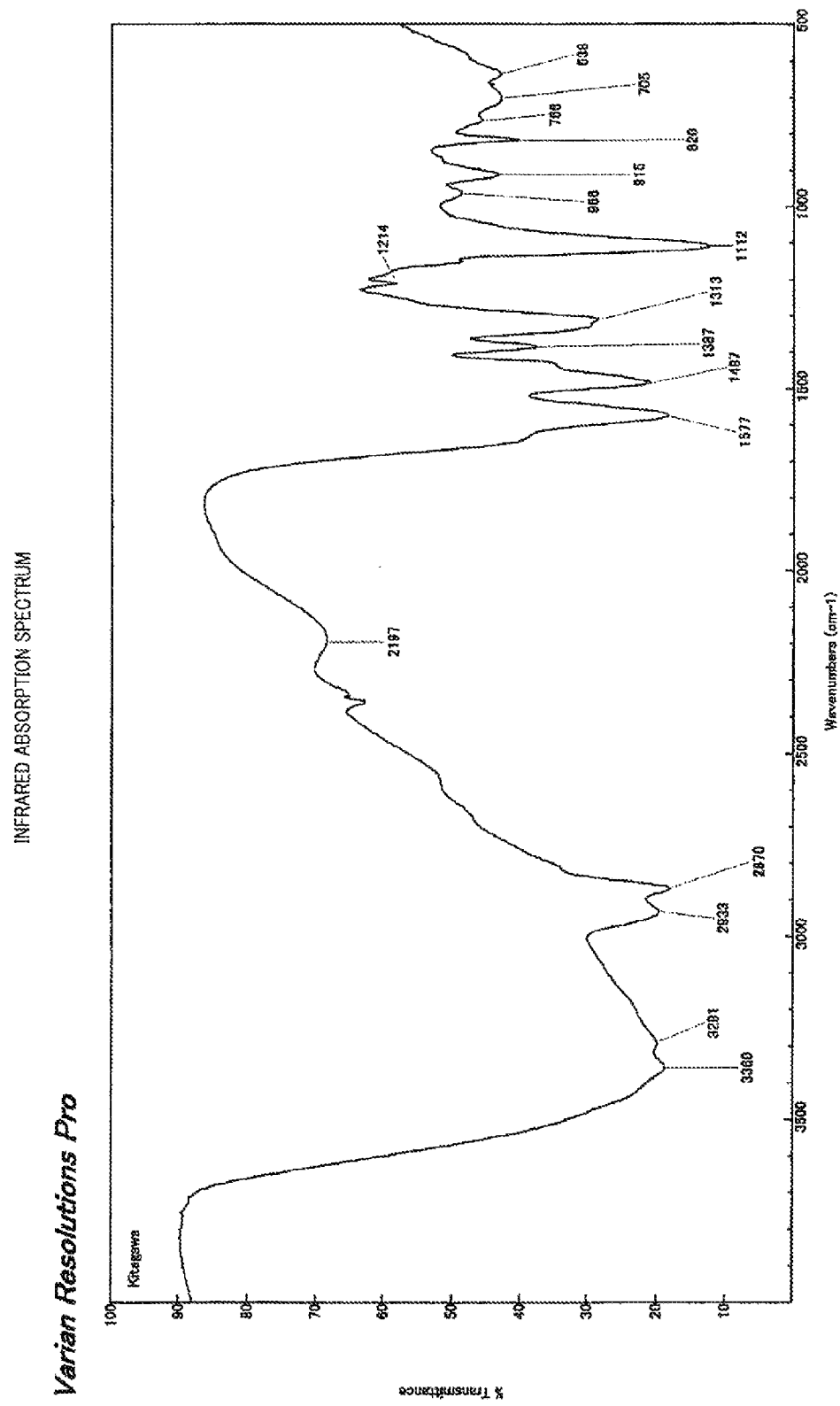
FIG. 3 is a diagram of an infrared absorption spectrum chart of a polyamine compound (1) which was synthesized in Example 1.

The obtained polyamine compound (1) was identified by using $^1$H-NMR spectrum, $^{13}$C-NMR spectrum and infrared absorption spectrum. The charts of identification data are shown in FIGS. 1 to 3. Here, the internal standard is TMS and the solvent for measuring is deuterated chloroform for both $^1$H-NMR spectrum and $^{13}$C-NMR spectrum.

Evaluation 1 of Epoxy Curing Properties 0.37 g of the obtained polyamine compound (1) and 1.70 g of 2,2-bis(4-glycidyloxyphenyl)propane (Tokyo chemical Industry Co., Ltd) were stirred and mixed thoroughly to prepare the sample liquid A. After the sample liquid A was left to stand at 25° C. for 3 days, it was confirmed that the sample liquid A was cured, by visual observation and tactile sensation.

Evaluation 2 of Epoxy Curing Properties 0.37 g of the obtained polyamine compound (1) and 1.01 g of 1,4-butane diglycidyl ether (Wako Pure Chemical Industries, Ltd) were stirred and mixed thoroughly to prepare the sample liquid B. After the sample liquid B was left to stand at 25° C. for 3 days, it was confirmed that the sample liquid B was cured, by visual observation and tactile sensation.

Evaluation 3 of Epoxy Curing Properties 0.37 g of the obtained polyamine compound (1) and 1.42 g of 1,2-cyclohexane dicarboxylic acid diglycidyl (Tokyo chemical Industry Co., Ltd) were stirred and mixed thoroughly to prepare the sample liquid C. After the sample liquid C was left to stand at 25° C. for 3 days, it was confirmed that the sample liquid C was cured, by visual observation and tactile sensation.

Example 2

Synthesis of Polyamine Compound (2)

The polyamine compound (2) ($R^1$ is a methyl group) of the present invention, represented by the general formula (3), was synthesized in the same manner as Example 1 except using 301.9 g (5.4 mol) of methacrylonitrile instead of 286.7 g (5.4 mol) of acrylonitrile in Example 1.

Evaluation 4 of Epoxy Curing Properties 0.426 g of the obtained polyamine compound (2) and 1.70 g of 2,2-bis(4-glycidyloxyphenyl)propane (Tokyo chemical Industry Co, Ltd) were stirred and mixed thoroughly to prepare the sample liquid D. After the sample liquid D was left to stand at 25° C. for 3 days, it was confirmed that the sample liquid D was cured, by visual observation and tactile sensation.

Example 3

According to the following scheme, the compound (hereinafter, referred to as a polyfunctional compound (1a)) in which $R^1$ and $R^3$ are a hydrogen atom in the polyfunctional compound represented by the general formula (4), was synthesized.

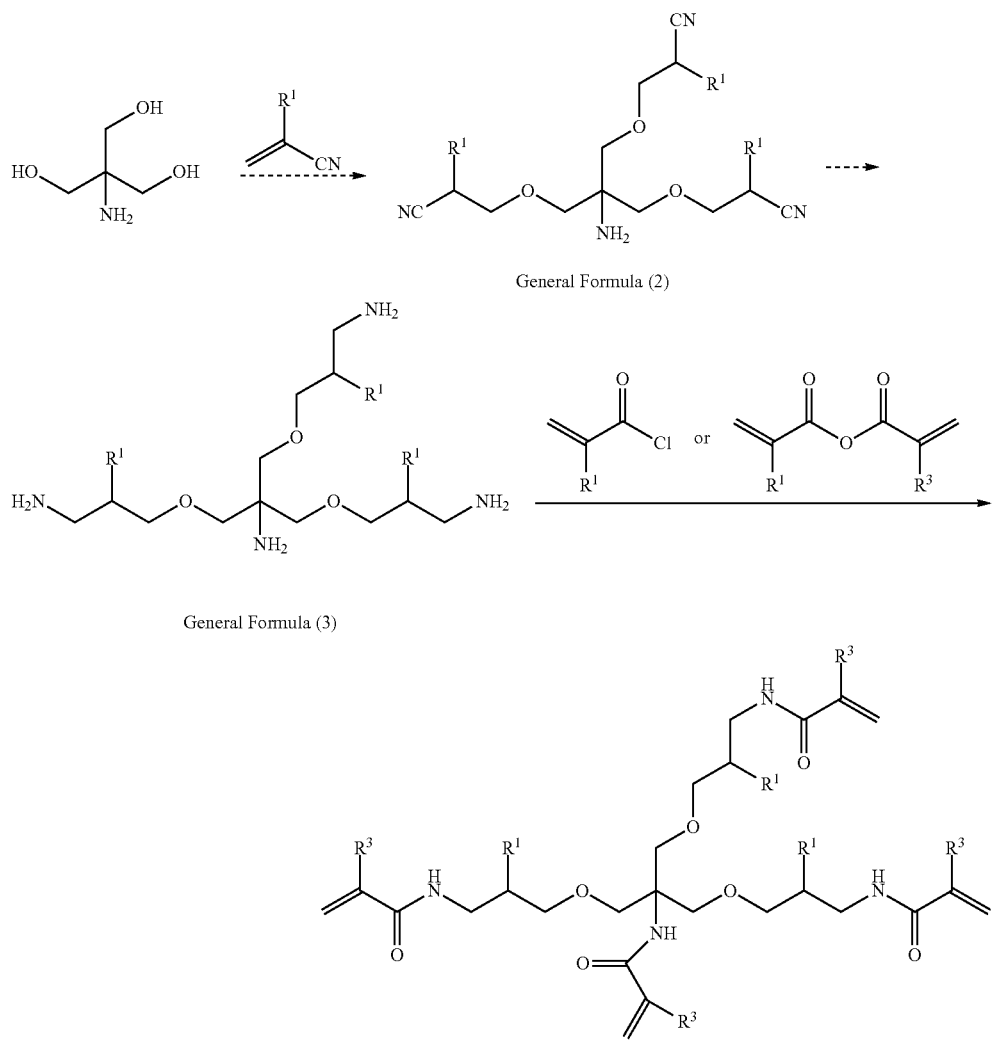

[Chem. 9]

General Formula (2)

General Formula (3)

General Formula (4)

[First Step]

121 g (1 equivalent) of tris(hydroxymethyl)aminomethane (manufactured by Tokyo Chemical Industry Co., Ltd.), 84 ml of 50% potassium hydroxide aqueous solution and 423 ml of toluene were added into a three-necked flask with a volume of 1 L, provided with a stirrer bar and stirred while maintaining the reaction system at 20° C. to 25° C. in an ice bath, and 397.5 g (7.5 equivalent) of acrylonitrile was added dropwise over 2 hours thereto. After the dropwise addition, the mixture was stirred for 1.5 hours, and then 540 ml of toluene was added into the reaction system. The obtained reaction mixture was transferred to a separatory funnel and water layer was removed. After drying the remaining organic layer using magnesium sulphate, the Celite filtration was conducted, and the intermediate (the acrylonitrile adduct) represented by general formula (2) was obtained by distilling off the solvent from the filtrate under reduced pressure. Since the result of analysis of the obtained acrylonitrile adduct by $^1$H-NMR and MS showed a good agreement with known products, the obtained acrylonitrile adduct was used in the next reduction reaction without further purification.

[Second Step]

24 g of the obtained acrylonitrile adduct, 48 g of the Ni catalyst (Raney nickel 2400, manufactured by W. R. Grace & Co.), and 600 ml of 25% aqueous ammonia:methanol=1:1 solution were put into an autoclave with a volume of 1 L and were suspended, and the reaction vessel was sealed. Hydrogen of 10 Mpa was introduced into the reaction vessel, and the reaction was conducted for 16 hours with a reaction temperature of 25° C.

The disappearance of the raw material (the acrylonitrile adduct) was confirmed by $^1$H-NMR, the obtained reaction mixture was filtrated by Celite filtration, and Celite was washed several times using methanol. The intermediate (the aminic body) represented by the general formula (3) was obtained by distilling off the solvent from the filtrate under reduced pressure. The obtained aminic body was used in the next reaction without further purification.

[Third Step]

(Synthesis of Polyfunctional Compound (1a))

30 g of the obtained aminic body, 120 g (14 equivalent) of NaHCO$_3$, 1 L of dichloromethane, and 50 ml of water were added into a three-necked flask with a volume of 2 L, provided with a stirrer, 92.8 g (10 equivalent) of acrylic acid chloride was added dropwise over 3 hours thereto in an ice bath, and thereafter, stirring was performed at room temperature for 3 hours. After the disappearance of the raw material (the aminic body) was confirmed by $^1$H-NMR, the solvent was distilled from the obtained reaction mixture under reduced pressure, the reaction mixture was dried using magnesium sulphate, and Celite filtration was performed with a solvent. Yellow liquid (yield of 40%) at normal temperature was obtained by distilling off the solvent from the obtained filtrate and purifying by using column chromatography (ethyl acetate:methanol=4:1).

The obtained yellow liquid was identified by $^1$H-NMR, $^{13}$C-NMR, IR and MS under measurement condition described below. The identification date is shown in FIGS. 4 to 7.

$^1$H-NMR solvent: Deuterated Chloroform, Internal standard: TMS $^{13}$C-NMR solvent: Deuterated Chloroform, Internal standard: TMS IR The reflectance spectrum was measured by applying the yellow liquid onto the copper foil, and was converted to absorbance.

MS solvent: MeOH/H$_2$O=9/1, 10 mM CH$_3$COONH$_4$

Figure 4:
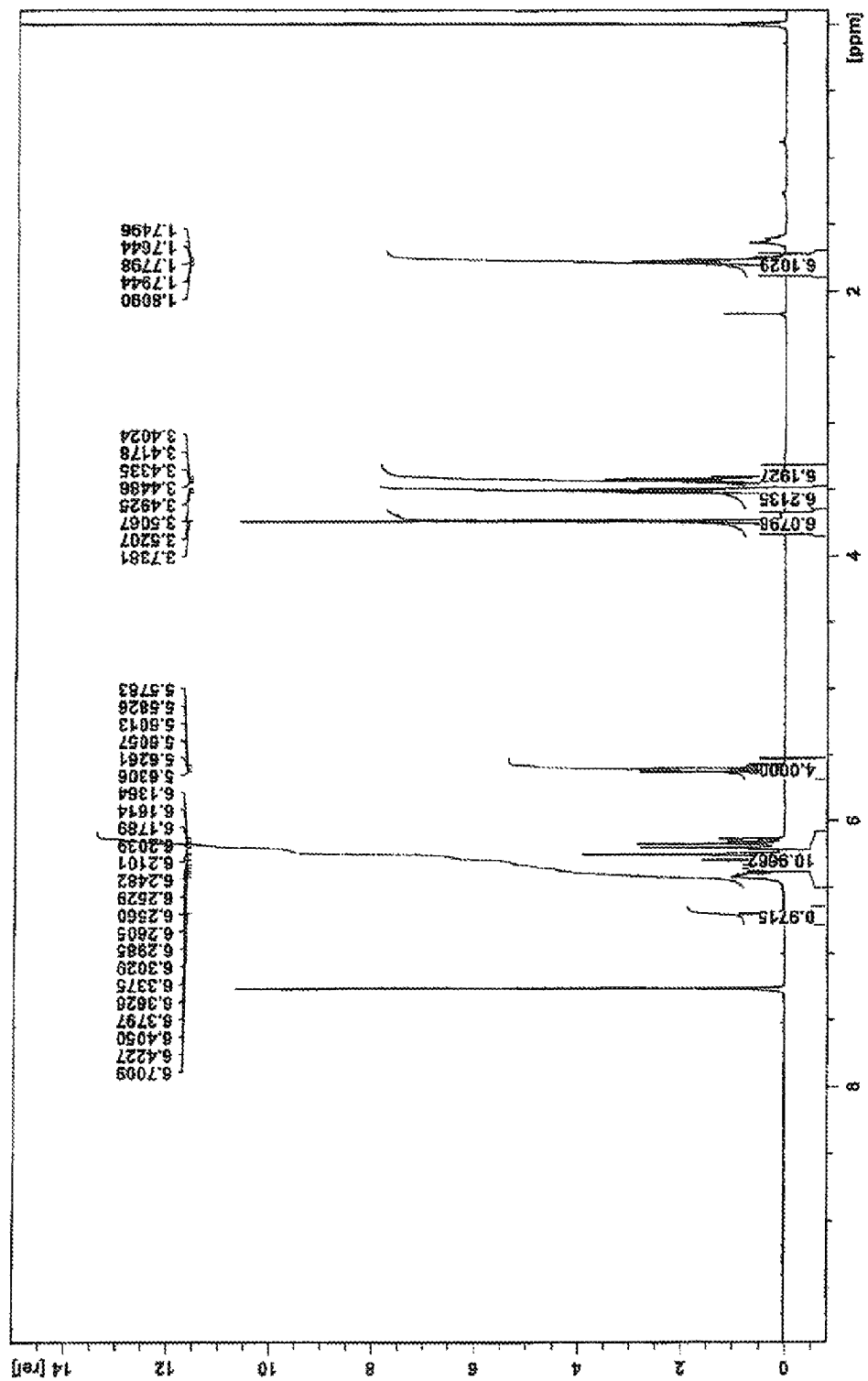
FIG. 4 is a diagram showing a $^1$H-NMR spectrum of a polyfunctional compound (1a) which was synthesized in Example 3.
Figure 5:
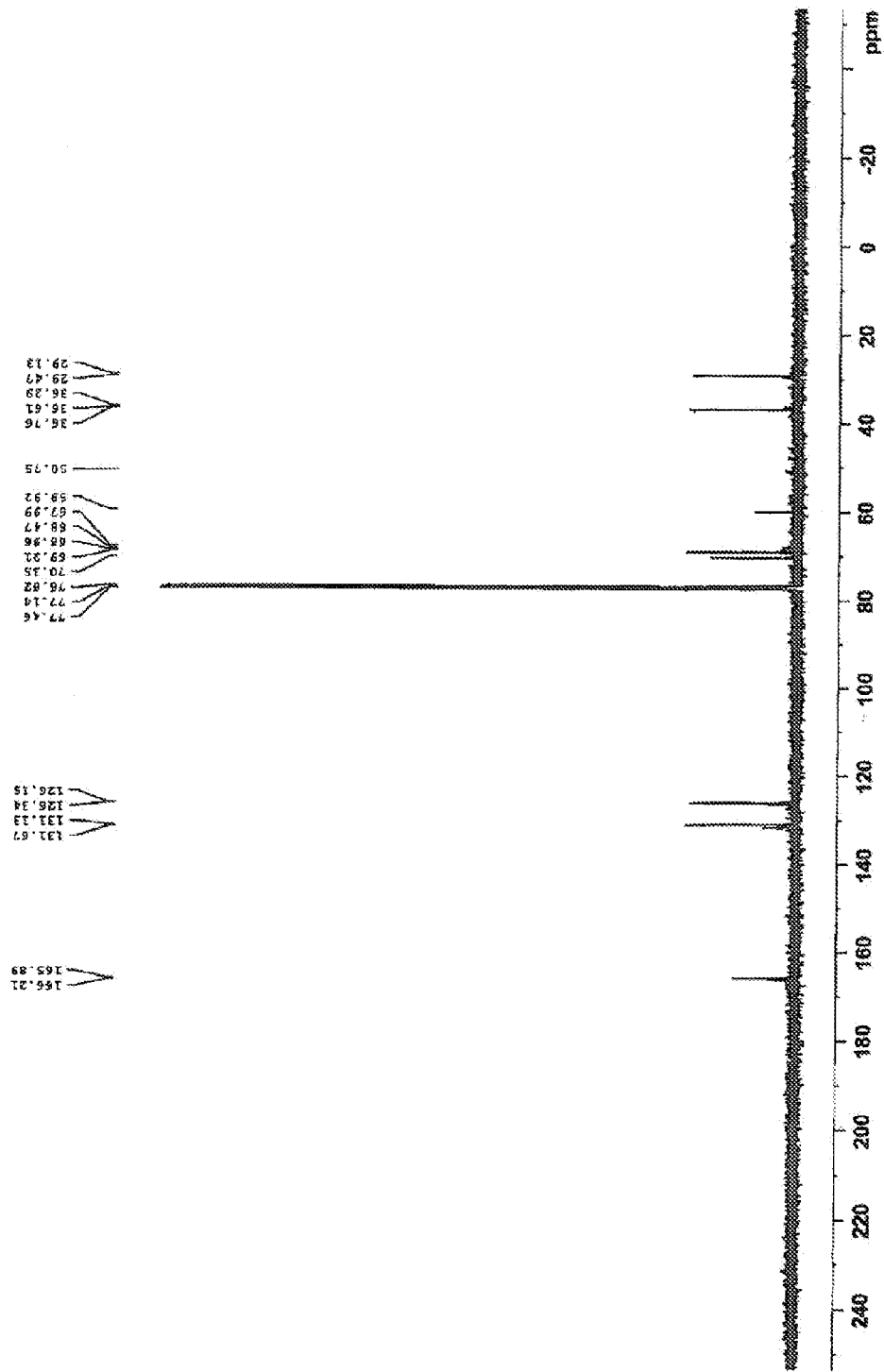
FIG. 5 is a diagram showing a $^{13}$C-NMR spectrum of a polyfunctional compound (1a) which was synthesized in Example 3
Figure 6:
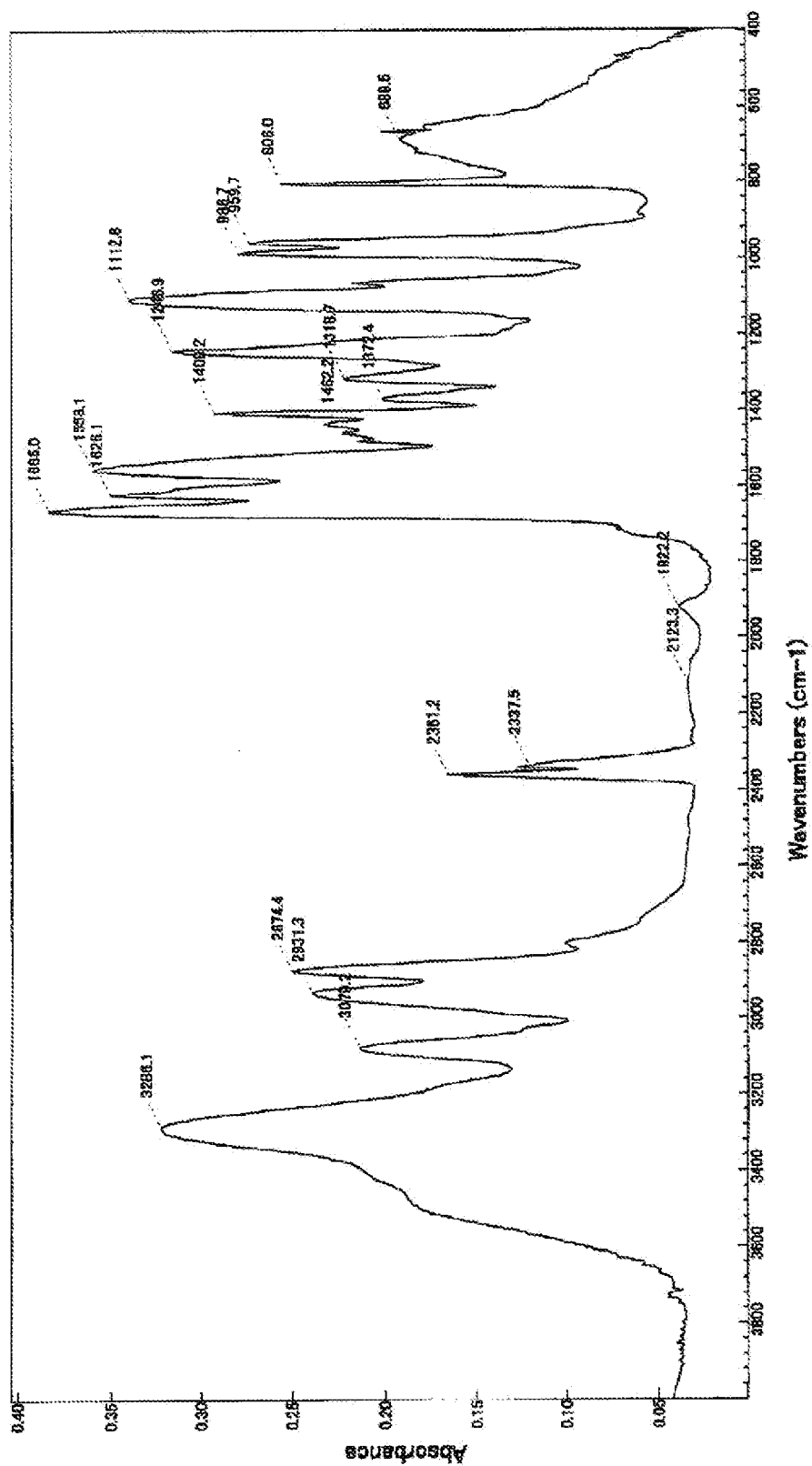
FIG. 6 is a diagram showing an infrared absorption spectrum of a polyfunctional compound (1a) which was synthesized in Example 3.
Figure 7:
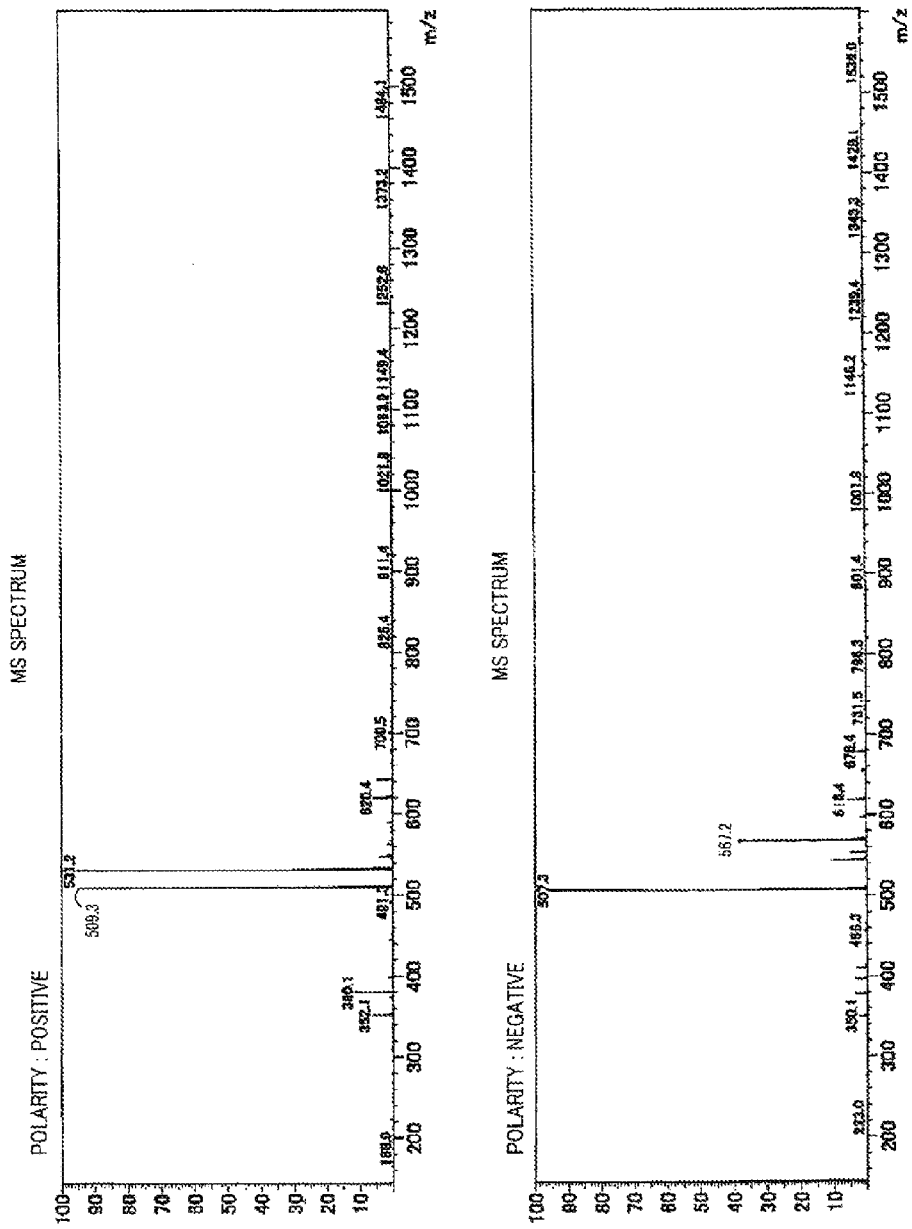
FIG. 7 is a diagram showing a result of analysis by MS of a polyfunctional compound (1a) which was synthesized in Example 3.

From the data of $^1$H-NMR shown in FIG. 4, since the integrated ratio of the peak of one hydrogen which was derived from acrylic near 5.6 ppm was 4 with respect to 6 of the integrated ratio of singlet peak (peak derived from the mother skeleton) near 3.75 ppm, it was found that the compound had four acrylic amide groups. From the data of $^{13}$C-NMR shown in FIG. 5, since the peaks of a carbonyl group and olefin were observed at characteristic positions and it was possible to confirm that the total carbon number was consistent with the number of total peaks, it was found that the compound had a structure represented by the polyfunctional compound (1a). In addition, from the data of IR shown in FIG. 6, it was found that the absorption of acrylamide was present. Furthermore, it was found that the molecular weight obtained from the data of MS shown in FIG. 7 was consistent with the molecular weight of the polyfunctional compound (1a).

From these results, it was confirmed that the yellow liquid obtained in Example 3 had a structure shown by the polyfunctional compound (1a) (the structure in which R$^1$ and R$^3$ are a hydrogen atom in the polyfunctional compound represented by the general formula (4), shown in the scheme described above)

Example 4

According to the scheme described above, the compound (hereinafter, referred to as a polyfunctional compound (1b)) in which R$^1$ is a hydrogen atom and R$^3$ is a methyl group in the polyfunctional compound represented by the general formula (4), was synthesized.

[First Step, Second Step]

The intermediate (the aminic body) represented by the general formula (3) was obtained in the same manner as the first step and the second step in Example 3. The obtained aminic body was used in the next reduction reaction without further purification.

[Third Step]

(Synthesis of Polyfunctional Compound (1b))

20 g of the obtained aminic body, 80.5 g (14 equivalent) of NaHCO$_3$, 684 ml of dichloromethane, and 32 ml of water were added into a three-necked flask with a volume of 2 L, provided with a stirrer, 105.5 g (10 equivalent) of dimethacrylic anhydride was added dropwise over 3 hours thereto in an ice bath, and after this, stirring was performed at room temperature for 12 hours. After the disappearance of the raw material (the aminic body) was confirmed by $^1$H-NMR, the solvent was distilled off under reduced pressure from the obtained reaction mixture, the reaction mixture was dried using magnesium sulphate, and Celite filtration was performed. Greenish yellow liquid (yield of 43%) at normal temperature was obtained by distilling off the solvent under reduced pressure from the obtained filtrate and purifying by using column chromatography (ethyl acetate/methanol=4:1)

The obtained greenish yellow liquid was identified under measurement condition described below by $^1$H-NMR, $^{13}$C-NMR, IR and MS. The identification date is shown in FIGS. 8 to 11.

$^1$H-NMR solvent: Deuterated Chloroform, Internal standard: TMS $^{13}$C-NMR solvent: Deuterated Chloroform, Internal standard: TMS IR The reflectance spectrum was measured by applying the greenish yellow liquid onto the copper foil, and was converted to absorbance.

MS solvent: MeOH/H$_2$O=9/1, 10 mM CH$_3$COONH$_4$

Figure 8:
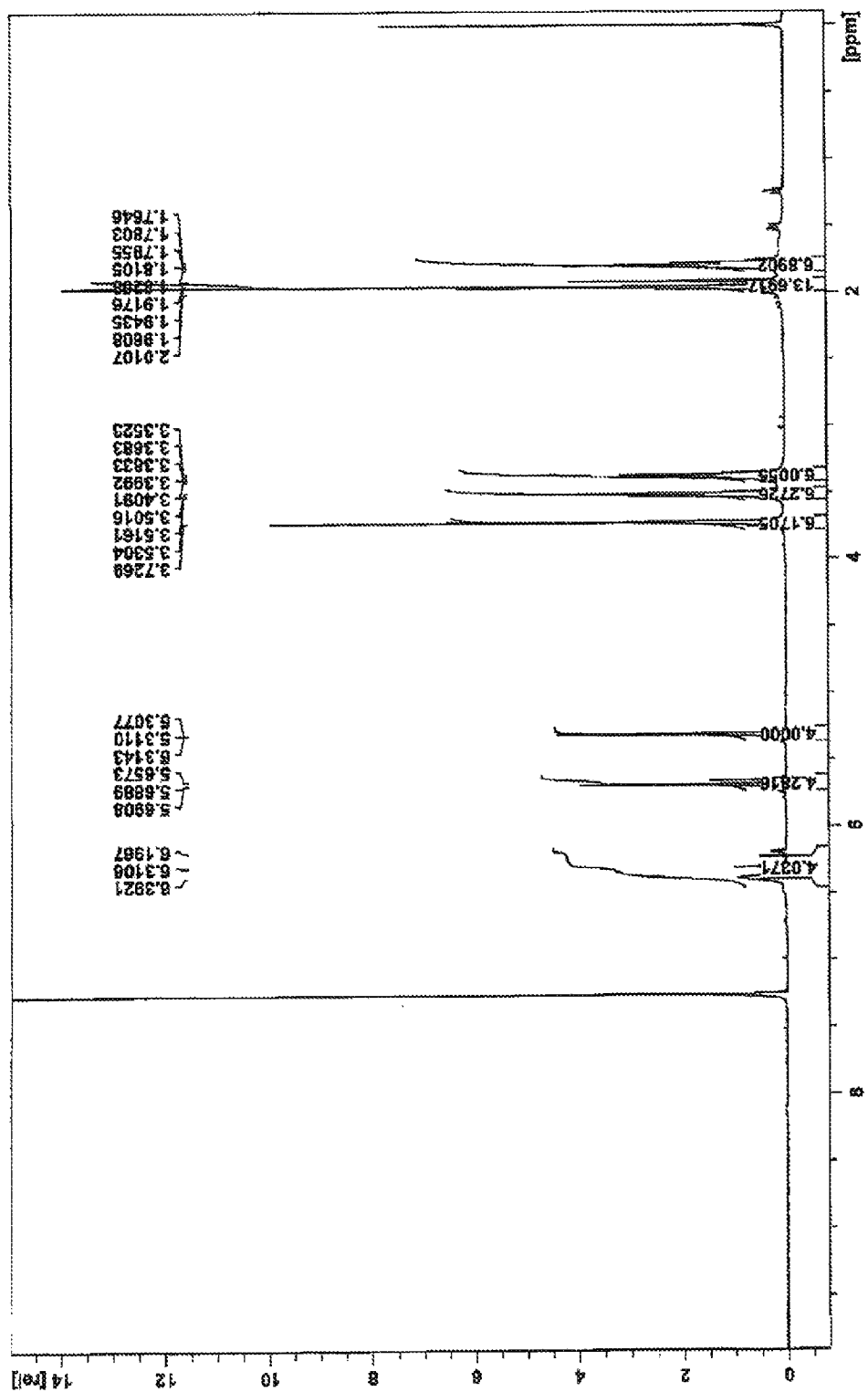
FIG. 8 is a diagram showing a $^1$H-NMR spectrum of a polyfunctional compound (1b) which was synthesized in Example 4.
Figure 9:
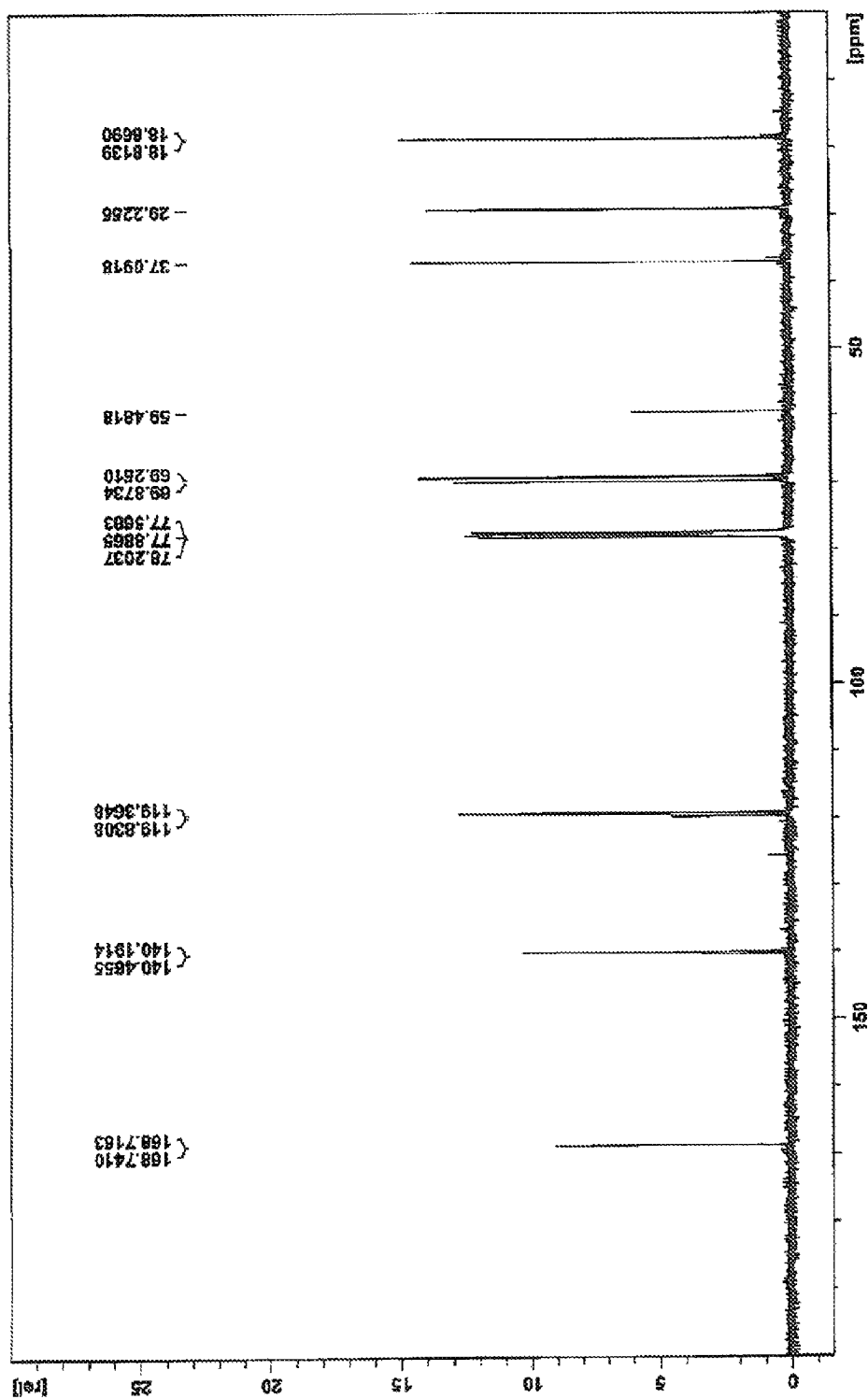
FIG. 9 is a diagram showing a $^{13}$C-NMR spectrum of a polyfunctional compound (1b) which was synthesized in Example 4.
Figure 10:
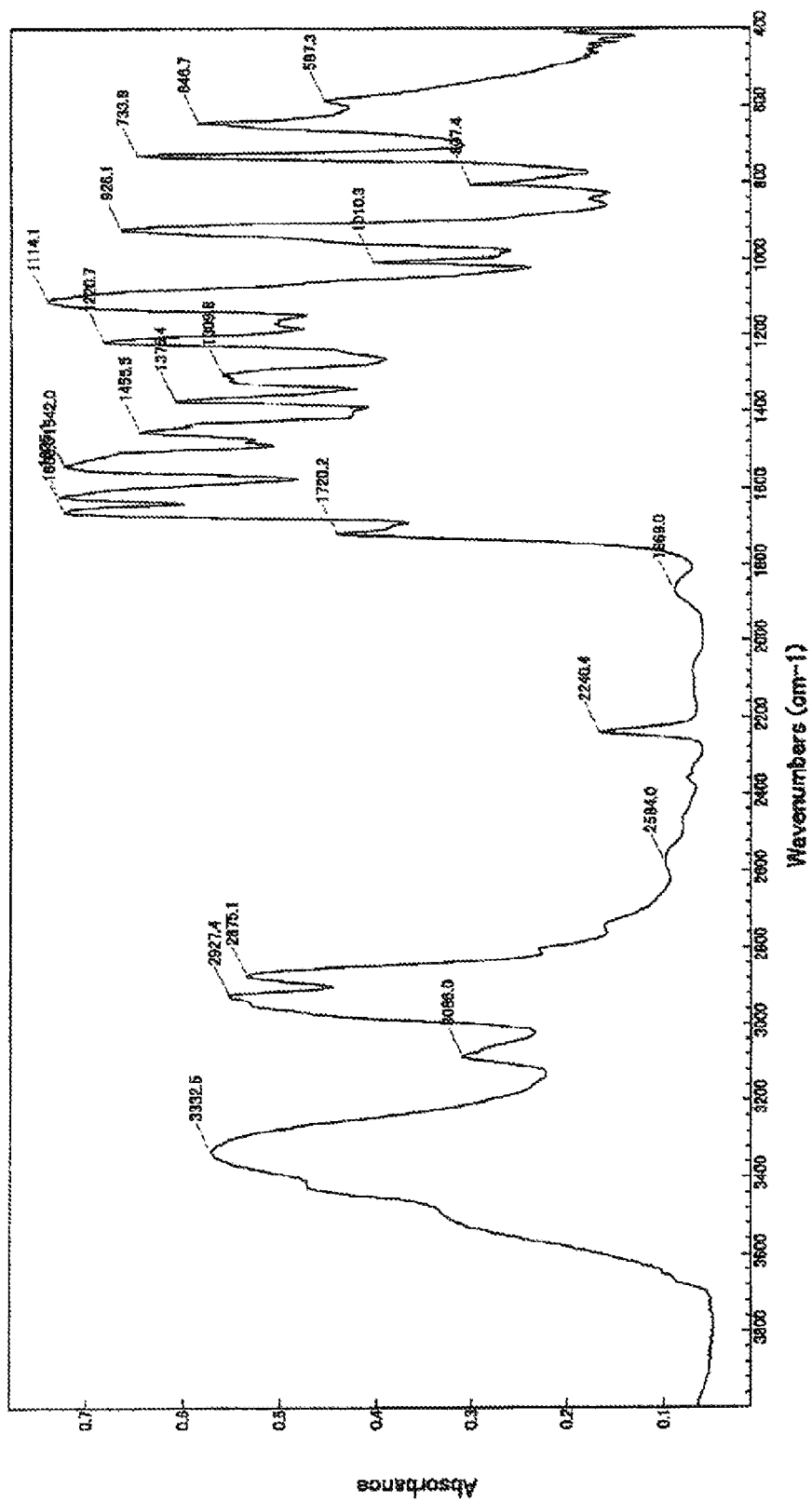
FIG. 10 is a diagram showing an infrared absorption spectrum of a polyfunctional compound (1b) which was synthesized in Example 4.
Figure 11:
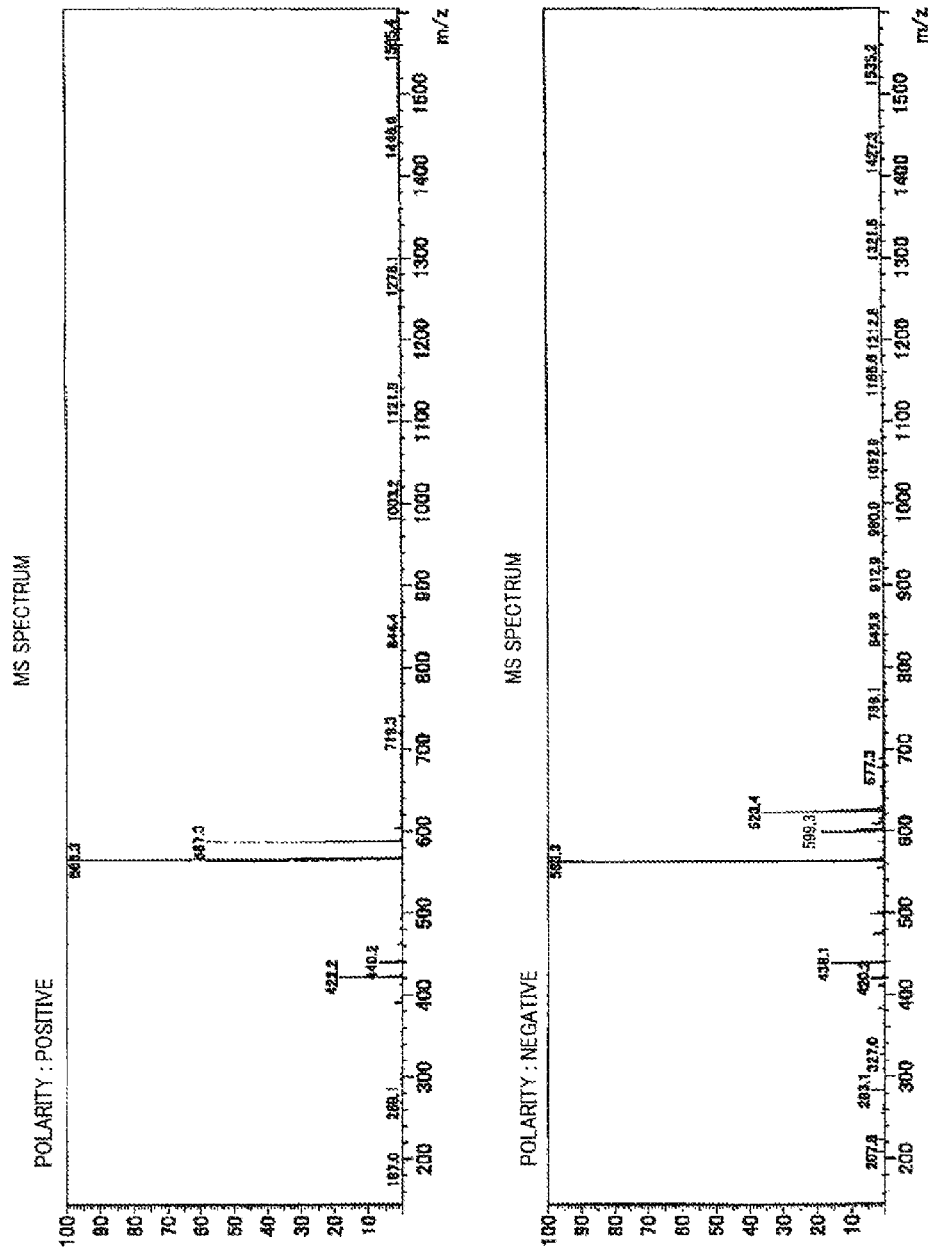
FIG. 11 is a diagram showing a result of analysis by MS of a polyfunctional compound (1b) which was synthesized in Example 4

From the data of $^1$H-NMR shown in FIG. 8, since the integrated ratio of the peak of one hydrogen which was derived from methacrylic near 5.3 ppm was 4, with respect to 6 of the integrated ratio of singlet peak (peak derived from the mother skeleton) near 3.72 ppm, it was found that the compound had four methacrylic amide groups. From the data of $^{13}$C-NMR shown in FIG. 9, since the peaks of a carbonyl group and olefin were observed at characteristic positions and it was possible to confirm that the total carbon number was consistent with the number of total peaks, it was found that the compound had a structure represented by the polyfunctional compound (1b). In addition, from the data of IR shown in FIG. 10, it was found that the absorption of methacrylamide was present. Furthermore, it was found that the molecular weight obtained from the data of MS shown in FIG. 11 was consistent with the molecular weight of the polyfunctional compound (1b).

From these results, it was confirmed that the greenish yellow liquid obtained in Example 4 had a structure shown by the polyfunctional compound (1b) (the structure in which $R^1$ is a hydrogen atom and $R^3$ is a methyl group in the polyfunctional compound represented by the general formula (4), shown in the scheme described above)

Evaluation of Curing Properties

The thermosetting properties of the polyfunctional compounds (1a) and (1b) synthesized in Examples 3 and 4 were evaluated in the following procedures.

The evaluation of curing properties was conducted by applying the sample solution consisting of the polyfuctional compound (1a) or (1b), a radical polymerizable initiator and an organic solvent onto a copper plate, heating this, and evaluating the progress of radical polymerization and the tactile sensation before and after heating. Here, the progress of radical polymerization was confirmed by observing the decrease in peak at 806 cm$^{-1}$ derived from an acrylic group by heating, by using FT-IR (VARIAN 3100 (trade name), manufactured by VARIAN Inc.) Details will be described below.

(Evaluation 1 of Curing Properties)

250 mg of the polyfunctional compound (1a) and 25 mg of AIBN (azobisisobutyronitrile) as a radical polymerization initiator were dissolved in 1 ml of methanol to prepare the sample liquid 1A for evaluation. 10 μl of this sample liquid 1A for evaluation was measured and taken out to apply onto a copper plate.

The copper plate applied with the sample liquid was measured by using FT-IR and the peak at 806 cm$^{-1}$ derived from an acryl group was confirmed. After this, the copper plate was heated at 100° C. for 1 hour using an oven under a nitrogen atmosphere. After heating, when the copper plate was measured again by using FT-IR, the peak at 806 cm$^{-1}$ derived from an acryl group was decreased. As a result of this, it was confirmed that the radical polymerization of the polyfunctional compound (1a) was progressed.

Furthermore, when the tactile sensation before and after heating was evaluated, there was no viscosity on the sample plate after heating, and there was no change as compared to before scrubbing even though scrubbing by a finger cushion. According to this, it was confirmed that the sample liquid applied onto the copper plate was cured by heating.

(Evaluation 2 of Curing Properties)

Subsequently, as to the polyfunctional compound (1b), the evaluation of curing properties were conducted by the same method as the polyfunctional compound (1a) described above. As a result of this, it was confirmed that the polyfunctional compound (1b) also had the same level of curing properties as the polyfunctional compound (1a).

What is claimed is:

1. A polyether compound represented by the following general formula (1),

[Chem. 1]

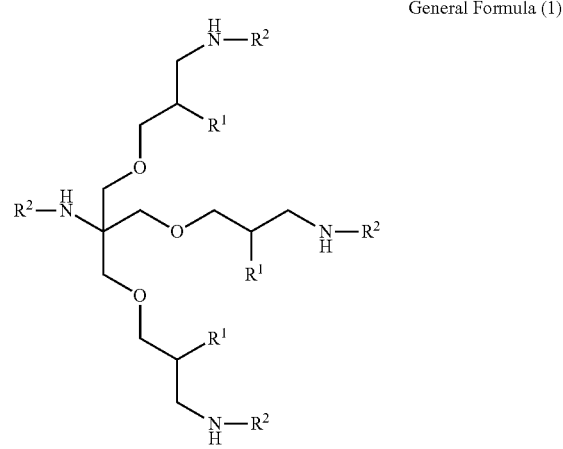

General Formula (1)

wherein, $R^1$ represents a hydrogen atom or a methyl group, $R^2$ represents a hydrogen atom or —C(=O)—C($R^3$)=CH$_2$, $R^3$ represents a hydrogen atom or a methyl group, and, $R^1$, $R^2$ and $R^3$ may be the same as or different from each other.

2. The polyether compound according to claim 1, wherein $R^2$ represents a hydrogen atom in the general formula (1).

3. The polyether compound according to claim 1, wherein $R^1$ represents a hydrogen atom and $R^2$ represents —C(=O)—C($R^3$)=CH$_2$ in the general formula (1).

4. A curing agent using the polyether compound according to claim 1.

5. A curing agent using the polyether compound according to claim 2.

6. A curing agent using the polyether compound according to claim 3.

7. A method for producing the polyether compound according to claim 1, comprising;

obtaining a compound represented by the following general formula (2) by reacting tris(hydroxymethyl)aminomethane with acrylonitrile and/or methacrylonitrile; and reducing the compound represented by the general formula (2),

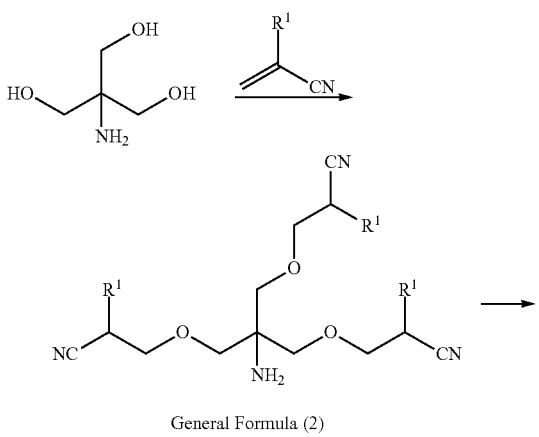

General Formula (2)

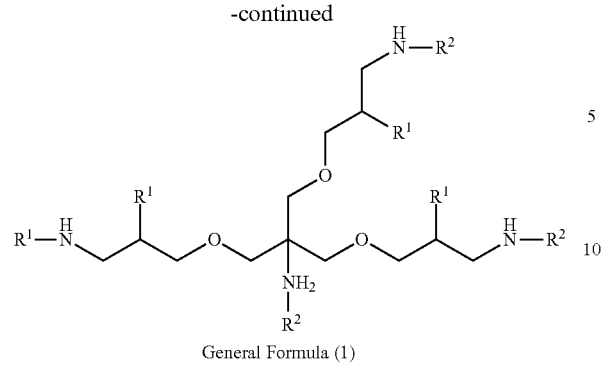
General Formula (1)
wherein, $R^1$ represents a hydrogen atom or a methyl group, $R^1$ may be the same as or different from each other, and $R^2$ represents a hydrogen atom.
* * * * *